United States Patent
Yates et al.

(10) Patent No.: US 11,039,896 B2
(45) Date of Patent: *Jun. 22, 2021

(54) ROBOTIC VISUALIZATION AND COLLISION AVOIDANCE

(71) Applicant: Ethicon LLC, Guaynabo, PR (US)

(72) Inventors: David C. Yates, West Chester, OH (US); Jason L. Harris, Lebanon, OH (US); Frederick E. Shelton, IV, Hillsboro, OH (US); Chad E. Eckert, Milford, OH (US)

(73) Assignee: Ethicon LLC, Guaynabo, PR (US)

(*) Notice: Subject to any disclaimer, the term of this patent is extended or adjusted under 35 U.S.C. 154(b) by 16 days.

This patent is subject to a terminal disclaimer.

(21) Appl. No.: 16/552,428

(22) Filed: Aug. 27, 2019

(65) Prior Publication Data

US 2019/0380799 A1  Dec. 19, 2019

Related U.S. Application Data

(63) Continuation of application No. 15/237,902, filed on Aug. 16, 2016, now Pat. No. 10,413,373.

(51) Int. Cl.
*A61B 34/00* (2016.01)
*A61B 34/37* (2016.01)
(Continued)

(52) U.S. Cl.
CPC ........ *A61B 34/37* (2016.02); *A61B 17/07207* (2013.01); *A61B 17/32* (2013.01); *A61B 34/30* (2016.02); *A61B 90/06* (2016.02); *A61B 2017/00017* (2013.01); *A61B 2017/00119* (2013.01); *A61B 2017/07271* (2013.01);
(Continued)

(58) Field of Classification Search
USPC .................................................. 700/245–264
See application file for complete search history.

(56) References Cited

U.S. PATENT DOCUMENTS

| | | | |
|---|---|---|---|
| 5,098,024 A | | 3/1992 | MacIntyre et al. |
| 5,737,500 A | * | 4/1998 | Seraji ............... B25J 9/1643 318/568.11 |

(Continued)

FOREIGN PATENT DOCUMENTS

| | | |
|---|---|---|
| EP | 2123216 A1 | 11/2009 |
| EP | 2414137 B1 | 6/2017 |
| WO | 2015125649 A1 | 8/2015 |

OTHER PUBLICATIONS

U.S. Appl. No. 15/131,963 entitled "Method for Operating a Surgical Instrument" filed Apr. 18, 2016.
(Continued)

*Primary Examiner* — Jonathan L Sample
(74) *Attorney, Agent, or Firm* — Mintz Levin Cohn Ferris Glovsky and Popeo, P.C.

(57) ABSTRACT

Methods and devices are provided for robotic surgery, and in particular for controlling various motions of a tool based on visual indicators. In general, a surgical tool can include an elongate shaft and an end effector coupled to a distal end of the elongate shaft and including first and second jaws. The tool can have at least one visual indicator disposed thereon and configured to indicate a size, position, or speed of movement of the tool or components of the tool.

20 Claims, 15 Drawing Sheets

(51) Int. Cl.
  *A61B 34/30* (2016.01)
  *A61B 17/072* (2006.01)
  *A61B 90/00* (2016.01)
  *A61B 17/32* (2006.01)
  *A61B 17/00* (2006.01)

(52) U.S. Cl.
  CPC ............... *A61B 2017/07278* (2013.01); *A61B 2017/07285* (2013.01); *A61B 2090/061* (2016.02); *A61B 2090/0811* (2016.02); *A61B 2090/3937* (2016.02)

(56) References Cited

U.S. PATENT DOCUMENTS

| | | | |
|---|---|---|---|
| 8,114,345 B2 | 2/2012 | Dlugos, Jr. et al. | |
| 8,882,792 B2 | 11/2014 | Dietz et al. | |
| 8,915,842 B2 * | 12/2014 | Weisenburgh, II | A61B 1/00091 600/156 |
| 8,931,682 B2 * | 1/2015 | Timm | A61B 17/068 227/178.1 |
| 8,945,098 B2 * | 2/2015 | Seibold | A61B 17/2909 606/1 |
| 9,498,231 B2 * | 11/2016 | Haider | A61B 5/1076 |
| 9,814,468 B2 | 11/2017 | Kang et al. | |
| 2001/0013764 A1 * | 8/2001 | Blumenkranz | A61B 34/70 318/568.11 |
| 2005/0043718 A1 * | 2/2005 | Madhani | A61B 34/77 606/1 |
| 2006/0258938 A1 * | 11/2006 | Hoffman | A61B 1/3132 600/424 |
| 2007/0144298 A1 * | 6/2007 | Miller | A61B 34/25 74/490.01 |
| 2008/0081948 A1 * | 4/2008 | Weisenburgh | A61B 1/3132 600/121 |
| 2009/0036902 A1 * | 2/2009 | DiMaio | A61B 34/30 606/130 |
| 2009/0245600 A1 * | 10/2009 | Hoffman | A61B 90/37 382/128 |
| 2009/0248036 A1 * | 10/2009 | Hoffman | A61B 1/00149 606/130 |
| 2010/0036393 A1 * | 2/2010 | Unsworth | A61B 34/76 606/130 |
| 2010/0168562 A1 * | 7/2010 | Zhao | A61B 90/94 600/426 |
| 2010/0168763 A1 * | 7/2010 | Zhao | A61B 90/94 606/130 |
| 2011/0118709 A1 * | 5/2011 | Burbank | A61B 17/00234 606/1 |
| 2011/0118778 A1 | 5/2011 | Burbank | |
| 2011/0245833 A1 * | 10/2011 | Anderson | B25B 23/0064 606/80 |
| 2011/0306873 A1 * | 12/2011 | Shenai | A61B 34/76 600/424 |
| 2012/0209288 A1 * | 8/2012 | Robinson | A61B 34/20 606/130 |
| 2013/0096574 A1 * | 4/2013 | Kang | A61B 34/37 606/130 |
| 2013/0172908 A1 * | 7/2013 | Sang | A61B 17/3494 606/130 |
| 2013/0253533 A1 * | 9/2013 | Bartol | A61B 34/30 606/130 |
| 2013/0282052 A1 * | 10/2013 | Aranyi | A61B 17/2816 606/208 |
| 2013/0325030 A1 * | 12/2013 | Hourtash | A61B 34/37 606/130 |
| 2014/0005718 A1 * | 1/2014 | Shelton, IV | A61B 34/35 606/205 |
| 2014/0168073 A1 * | 6/2014 | Chizeck | G06F 3/016 345/156 |
| 2014/0214204 A1 | 7/2014 | Toshimitsu et al. | |
| 2014/0275955 A1 * | 9/2014 | Crawford | A61B 5/061 600/409 |
| 2015/0223897 A1 * | 8/2015 | Kostrzewski | A61B 46/10 606/130 |
| 2015/0248121 A1 | 9/2015 | Nilsson | |
| 2015/0366624 A1 * | 12/2015 | Kostrzewski | A61M 29/00 606/130 |
| 2016/0128781 A1 * | 5/2016 | Blohm | A61B 34/30 606/130 |
| 2016/0129595 A1 * | 5/2016 | Gerio | B25J 13/086 700/255 |
| 2018/0049829 A1 * | 2/2018 | Yates | A61B 34/37 |
| 2018/0049830 A1 * | 2/2018 | Yates | A61B 34/35 |

OTHER PUBLICATIONS

U.S. Appl. No. 15/177,430 entitled "Surgical Instrument With User Adaptable Techniques" filed Jun. 9, 2016.

* cited by examiner

ROBOTIC VISUALIZATION AND COLLISION AVOIDANCE

CROSS REFERENCE TO RELATED APPLICATION

This application is a continuation of U.S. patent application Ser. No. 15/237,902 (now U.S. Pat. No. 10,413,373) filed Aug. 16, 2016, entitled "Robotic Visualization and Collision Avoidance," which is hereby incorporated herein by reference in its entirety.

FIELD OF THE INVENTION

Methods and devices are provided for robotic surgery, and in particular for visualizing, controlling, and collision avoidance in robotic tools.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

Robotic surgical systems are typically controlled by an operator operating the various components from a terminal. The controller, based on their view of the robot and based on readouts presented on a screen of the terminal can control the components and avoid collisions between the robotic components. While significant advances have been made in the field of robotic surgery, there remains a need for improved methods, systems, and devices for use in robotic surgery to improve visualization and control over components while avoiding accidental collisions and reducing human error in surgical procedures.

SUMMARY OF THE INVENTION

Methods and devices are provided for robotic surgery, and in particular for communicating with and controlling robotic tools including end effectors.

In one aspect, a surgical robotic system is provided that includes an electromechanical arm configured for movement in multiple axes and an electromechanical tool configured to couple to the electromechanical arm that has an elongate shaft with an end effector coupled to a distal end thereof. The system includes a controller that is configured to control movement of the electromechanical arm and to control actuation of the end effector on the electromechanical tool. The electromechanical tool includes at least one visual indicator indicative of a length scale that is effective to allow an action of the end effector to be visually measured. The controller is configured to modify the action of the end effector based on the visually measured action.

The system can vary in a number of ways. For example, the end effector can include a cutting element that is advanced through the end effector. The at least one visual indicator can also be configured to indicate a travel speed of the cutting element. The at least one visual indicator can include a plurality of markings spaced apart along at least one of the shaft and the end effector. In another example, the at least one visual indicator can include a grid pattern formed on the end effector. In still another example, the end effector can include a cutting element that is advanced through the end effector and a plurality of cut-outs that are formed in the end effector, enabling viewing of the cutting element therethrough as the cutting element is advanced through the end effector. The cutting elements can also include a grid pattern formed therein that is visible through the plurality of cut-outs. In another example, the electromechanical tool can include a housing on a proximal end of the shaft that couples to a tool driver on a distal end of the electromechanical arm. The tool driver can include a plurality of motors for actuating the end effector. The system can also include at least one camera configured to visually measure the action of the end effector.

In another aspect, a robotic system is provided that includes a tool housing with a plurality of gear assemblies. Each gear assembly is configured to couple to a motor on a tool driver. An elongate shaft extends distally from the tool housing. An end effector with first and second jaws pivotably coupled thereto extends from a distal end of the elongate shaft. At least one visual indicator is disposed on the end effector, and at least one camera is configured to visually monitor the visual indicator. The system also includes a controller that is configured to provide a declared action of the end effector and that is configured to compare the declared action with an actual action of the end effector based on detection of the visual indicator by the at least one camera.

The robotic system can have numerous variations. For example, the controller can also be configured to compare an actual speed of advancement of a cutting element moving through the end effector to a threshold speed, and to decrease a speed of the cutting element when the actual speed reaches the threshold speed. In another example, the at least one visual indicator includes a grid pattern formed on the end effector. The at least one visual indicator can also include openings along at least one of the first and second jaws of the end effector. The at least one camera can be configured to view motion of a cutting element through the openings. The at least one visual indicator can also be indicative of a length scale. The robotic system can also include a proximity zone at a distal end of the end effector. The controller can be configured to reduce a speed of advancement of a cutting element through the end effector when the cutting element reaches the proximity zone.

In another aspect, a surgical method is provided that includes causing a controller on a surgical robotic system to transmit input instructions to an electromechanical tool to thereby actuate the tool. The surgical robotic system visually obtains information from a visual indicator on the tool indicative of a length scale. If the visually obtained information differs from the input instructions, the controlled transmits altered input instructions to the electromechanical tool based on the visually obtained information.

The method can vary in a number of ways. For example, the input instructions can cause a cutting element to travel through an end effector of the tool at a first travel speed, and the visual indicator can indicate an actual travel speed of the sled. The altered input instructions can also include a reduced travel speed if the actual travel speed exceeds a threshold travel speed. In another example, the visual indicator can include at least one marking formed on an end effector of the tool and configured to indicate a length scale of the tool.

In an aspect, a surgical robot system is provided including a robotic arm with a proximal end configured to couple to a support and having a distal end with a driver including at least one motor. A tool housing is configured to releasably couple to the driver, and an elongate shaft extends distally from the housing. An end effector is disposed on a distal end of the elongate shaft. At least one position sensor is configured to detect at least one of a position and a velocity of the end effector within a three-dimensional space. The system is configured to reduce a velocity of the end effector when the at least one of the position and the velocity of the end effector exceeds a threshold boundary.

The system can vary in a number of ways. For example, the system can include at least one actuator that is configured to actuate the end effector. The actuator can be configured to retard motion of the end effector in response to an output received from the position sensor indicating that the end effector is at a predetermined location within a three dimensional space. The at least one position sensor can also be configured to detect a proximity of a second tool within a three dimensional space and to output a signal indicating the proximity of the second tool relative to the end effector. In another example, the at least one position sensor can include an electromagnetic sensor that can be configured to detect a position of a magnetic material on the second tool. The electromagnetic sensor can be configured to detect perturbations in a magnetic field caused by the additional electromechanical tool within the electromagnetic field. In another example, the position sensor can be configured to detect a strength of a magnetic field emitted by an magnetic field emitter, and the actuator can be configured to retard the motion of the electromechanical tool in response to a detection by the position sensor that the electromechanical tool is at a position in the three dimensional space having a predetermined magnetic field strength. The position sensor can also be at least one camera configured to obtain images of the electromechanical sensor. The threshold boundary can be configured to be changed by a user. In another example, the system can also include a second robotic tool with a second end effector that includes a second position sensor configured to detect the position of the second end effector in a three dimensional space. The position sensor can be configured to communicate with the second position sensor.

In another embodiment, a surgical robotic system can be provided that includes an electromechanical arm configured for movement in multiple axes. An electromechanical tool is configured to couple to the electromechanical arm and has an elongate shaft with an end effector coupled to a distal end thereof. A controller is configured to control movement of the electromechanical arm and to control actuation of the end effector on the electromechanical tool. The electromechanical tool includes a pre-set motion control threshold, and the controller is configured to prevent the electromechanical tool from exceeding the pre-set motion control threshold when the controller actuates at least one of the electromechanical arm and the electromechanical tool.

The system can vary in a number of ways. For example, the pre-set motion control threshold can include a threshold velocity of the end effector. The system can also include a second electromechanical tool with a second pre-set motion control threshold. The controller can be configured to actuate at least one of a second electromechanical arm and the second electromechanical tool and can be configured to prevent the second electromechanical tool from exceeding the second pre-set motion control threshold when the controller actuates at least one of the second electromechanical arm and the second electromechanical tool. In another example, at least one of the pre-set motion control threshold and the second pre-set motion control threshold can be configured to be changed by a user. The system can also include a proximity sensor that can be configured to detect and to output a signal indicating a proximity of the end effector to any surrounding objects. The system can include an electromagnetic sensor that can be configured to detect a position of a magnetic material on the end effector. The system can also include at least one camera that can be configured to obtain images of the electromechanical tool.

In another aspect, a surgical method is provided that includes causing a controller on a surgical robotic system to transmit input instructions to an electromechanical tool to thereby move the tool. The electromechanical tool has a pre-set motion control threshold, and the controller is configured to prevent the electromechanical tool from exceeding the pre-set motion control threshold when the controller moves the tool.

The method can have numerous variations. For example, the method can include causing the controller to transmit input instructions to a second electromechanical tool to thereby move the second electromechanical tool. The second electromechanical tool can have a second pre-set motion control threshold, and the controller can be configured to prevent the second electromechanical tool from exceeding the second pre-set motion control threshold when the controller moves the second electromechanical tool. The pre-set motion control threshold can also include a threshold velocity of the end effector.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
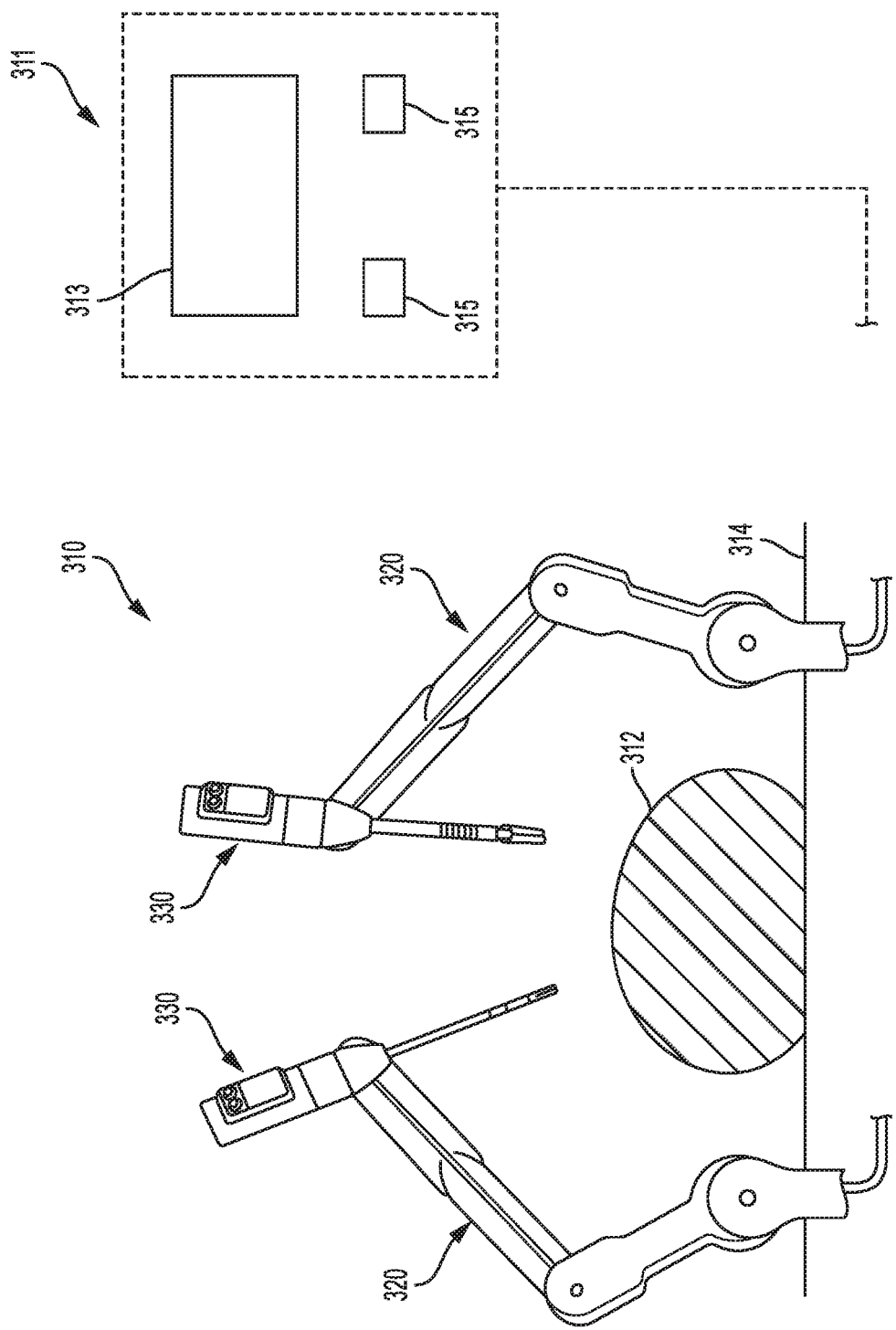
FIG. 1 is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Generally robotic surgical systems have surgical tools with one or more moving components operated remotely in a human body. Any actuation of the tool(s) and/or moving components on the tool(s) includes risks of damaging the tool(s) and/or causing harm to a patient while the tool(s) are being used. Accordingly, visual indicators are provided with the robotic surgical systems and/or on the surgical tools to visually obtain certain information concerning the surgical tools, actuation and behavior of the tools within the patient, and their location within the patient. That information is used to control actuation of the tools, such as rotation, articulation, clamping, cutting, suturing, energy delivery, etc. and/or to control movement of the tool within the patient's body relative to tissue and/or other tools. Visual indicators can take a variety of forms, such as markings on or around a surgical tool and/or tissue that indicate size, position, motion, etc., visualization of parts of the surgical tool, and/or visualization of parts of the tissue. The one or more visual indicators associated with a robotic surgical system can provide feedback to the robotic surgical system, which can modify tool actuation and/or movement based on the feedback provided.

In one embodiment, an end effector can have at least one visual indicator disposed thereon, such as an indicator for indicating a length scale of the end effector and that is effective to allow an action of the end effector to be visually measured. The robotic system can modify the action of the end effector based on the visually measured action. For example, methods, systems, and devices are provided for visually determining a position of various movable features on an end effector, such as a cutting element on an end effector. In some embodiments, a cutting element can be configured to advance through jaws on an end effector to cut tissue engaged therebetween. In such embodiments, an indicator can be configured to allow a position of the cutting element relative to the end effector to be detected. The indicator(s) can also allow calculation of a position and/or speed of the cutting element relative to the end effector. The position and/or the speed of the cutting element can be calculated to determine if the speed of the cutting element should be adjusted to ensure that tissue grasped between the jaws is cleanly cut and to ensure that the cutting element is not advanced at a high rate of speed into a distal end of the end effector. For example, a threshold speed can be set, and the speed of the sled can be monitored to ensure that the speed does not exceed the threshold speed. If tissue grasped between the jaws is too thick, the sled or cutting element is in danger of being advanced too rapidly through the end effector, causing uneven, incomplete, or ragged cuts in the grasped tissue. Additionally, if the sled advances too rapidly, the sled can impact a distal end of the end effector at a high rate of speed instead of coming to an appropriate stop. By detecting the actual position and/or speed of the sled using visual markings, an appropriate speed can be maintained, limiting or preventing harm to a patient and ensuring a more successful cut and seal to tissue. This can be particularly important for cutting elements that do not maintain a pre-set distance between the two jaws. While an example of advancing a cutting element is provided above, any type of end effector can be used with any type of action, such as grasping, suturing, stapling, cutting, applying energy, etc.

Visualization of one or more markings during use of a surgical robotic system can also be used with multiple tools, as well. For example, many robotic surgical systems have multiple surgical tools that are manipulated by the surgeon, often simultaneously. The tools are often in close proximity to each other and can inadvertently collide with each other and/or surrounding tissue. Collisions, even at slow speeds, can cause damage to the precision components of the robotic surgical system, and also can cause unintentional damage to tissue that the components of the robotic surgical systems are interacting with. For instance, if a robotic surgical system is holding tissue by using a clamp, the impact from a collision can cause the tissue to tear. Similarly, if the robotic surgical system is cutting tissue with a knife, the impact could cause an inadvertent cut in the tissue.

Robotic surgical systems are thus provided in which a velocity of a tool being moved by a robotic arm can be reduced if the tool is within a threshold distance from another tool or a tissue surface, as detected by visualizing one or more indicators on the tools and/or tissue. In certain aspects, there can be multiple threshold distances where the closer the tool gets to another object the more the velocity of the tool, as controlled by the robotic arm, is reduced. At a certain close proximity to another object or tool, the robotic arm can be configured to halt movement toward the other object or the tool. The robotic surgical system can also be configured to allow an operator of the robotic surgical system to move the robotic arms beyond the threshold further toward the object or other tool. In other aspects, the robotic surgical system can be configured to gradually move two tools toward each other at a reduced velocity in response to an input by an operator indicating a desire to move the robotic arms simultaneously.

The systems, devices, and methods disclosed herein can be implemented using a robotic surgical system. FIG. 1 is a perspective view of one embodiment of a surgical robotic system 300 that includes a patient-side portion 310 that is positioned adjacent to a patient 312, and a user-side portion 311 that is located a distance from the patient, either in the same room and/or in a remote location. The patient-side portion 310 generally includes one or more robotic arms 320 and one or more tool assemblies 330 that are configured to releasably couple to a robotic arm 320. The user-side portion 311 generally includes a vision system 313 for viewing the patient 312 and/or surgical site, and a control system 315 for controlling the movement of the robotic arms 320 and each tool assembly 330 during a surgical procedure.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 310 and/or to control one or more parts of the patient-side portion 310 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 320 and tool assemblies 330.

The patient-side portion can also have a variety of configurations. As depicted in FIG. 1, the patient-side portion 310 can couple to an operating table 314. However, in some embodiments, the patient-side portion 310 can be mounted to a wall, to the ceiling, to the floor, or to other operating room equipment. Further, while the patient-side portion 310 is shown as including two robotic arms 320, more or fewer robotic arms 320 may be included. Furthermore, the patient-side portion 310 can include separate robotic arms 320 mounted in various positions, such as relative to the surgical table 314 (as shown in FIG. 1). Alternatively, the patient-side portion 310 can include a single assembly that includes one or more robotic arms 320 extending therefrom.

Figure 2:
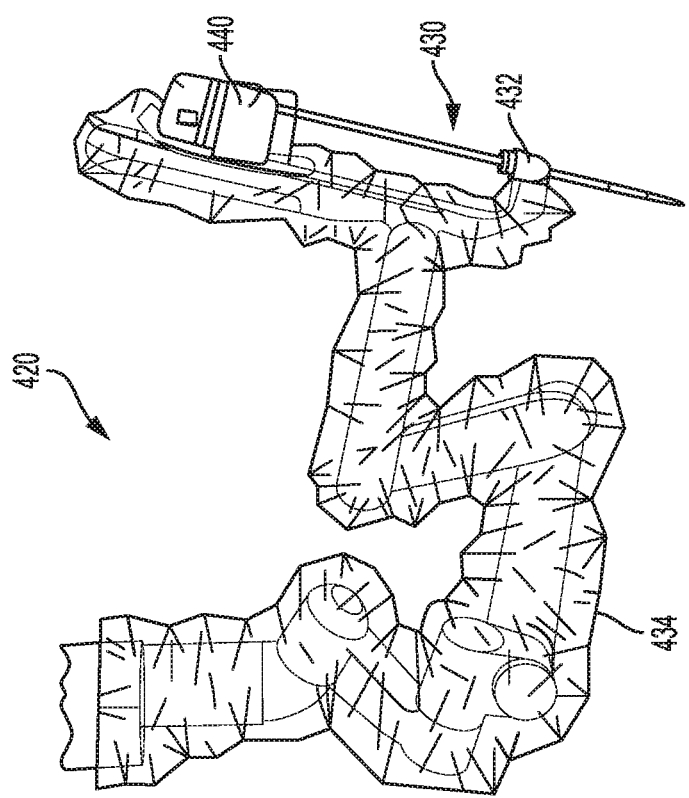
FIG. 2 is a perspective view of an embodiment of a robotic arm of a surgical robotic system with a tool assembly releasably coupled to the robotic arm.

FIG. 2 illustrates one embodiment of a robotic arm 420 and a tool assembly 430 releasably coupled to the robotic arm 420. The robotic arm 420 can support and move the associated tool assembly 430 along one or more mechanical degrees of freedom (e.g., all six Cartesian degrees of freedom, five or fewer Cartesian degrees of freedom, etc.).

The robotic arm 420 can include a tool driver 440 at a distal end of the robotic arm 420, which can assist with controlling features associated with the tool assembly 430. The robotic arm 420 can also include an entry guide 432 (e.g., a cannula mount or cannula) that can be a part of or removably coupled to the robotic arm 420, as shown in FIG. 2. A shaft 436 of the tool assembly 430 can be inserted through the entry guide 430 for insertion into a patient.

In order to provide a sterile operation area while using the surgical system, a barrier 434 can be placed between the actuating portion of the surgical system (e.g., the robotic arm 420) and the surgical instruments (e.g., the tool assembly 430). A sterile component, such as an instrument sterile adapter (ISA), can also be placed at the connecting interface between the tool assembly 430 and the robotic arm 420. The placement of an ISA between the tool assembly 430 and the robotic arm 420 can ensure a sterile coupling point for the tool assembly 430 and the robotic arm 420. This permits removal of tool assemblies 430 from the robotic arm 420 to exchange with other tool assemblies 430 during the course of a surgery without compromising the sterile surgical field.

Figure 3:
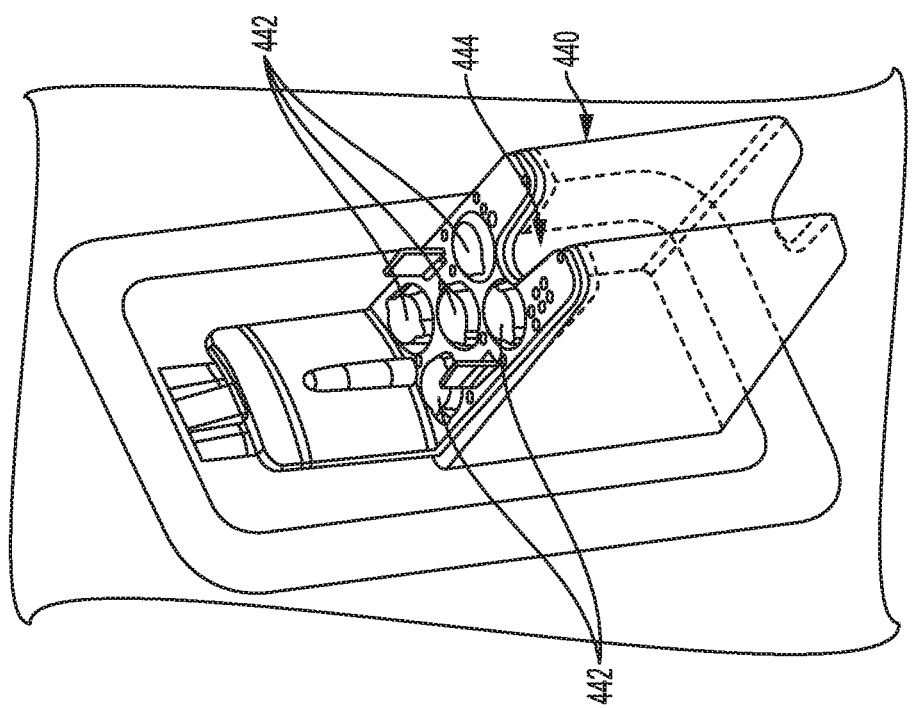
FIG. 3 is a perspective view of a tool driver of the robotic arm of FIG. 2.

FIG. 3 illustrates the tool driver 440 in more detail. As shown, the tool driver 440 includes one or more motors, e.g., five motors 442 are shown, that control a variety of movements and actions associated with the tool assembly 430, as will be described in greater detail below. For example, each motor 442 can couple to and/or interact with an activation feature (e.g., gear) associated with the tool assembly 430 for controlling one or more actions and movements that can be performed by the tool assembly 430, such as for assisting with performing a surgical operation. The motors 442 are accessible on the upper surface of the tool driver 440, and thus the tool assembly is configured to mount on top of the tool driver 440 to couple thereto. The tool driver 440 also includes a shaft-receiving channel 444 formed in a sidewall thereof for receiving the shaft of the tool assembly 430. In other embodiments, the shaft can extend through an opening in the tool driver 440, or the two components can mate in various other configurations.

Figure 4:
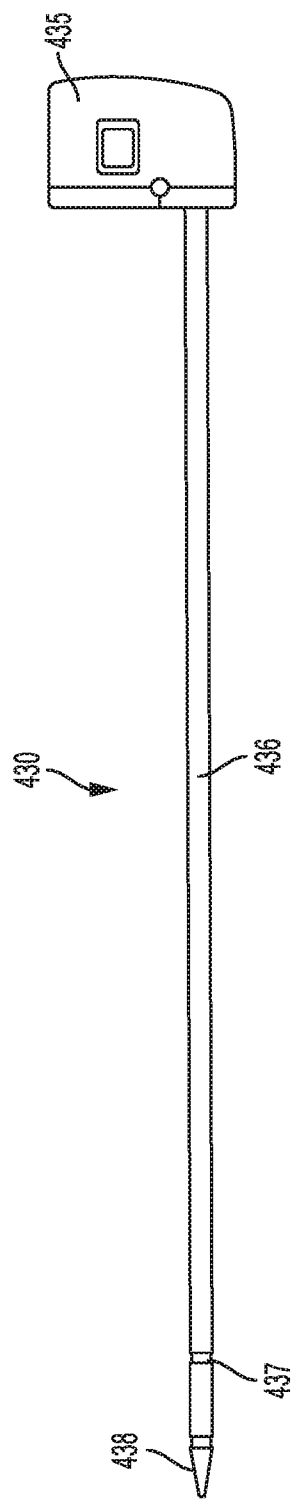
FIG. 4 is a side view of the tool assembly of FIG. 2 uncoupled from the robotic arm, the tool assembly including a shaft extending from a tool housing at a proximal end and having an end effector located at a distal end of the shaft.

FIG. 4 illustrates the tool assembly 430 uncoupled from the robotic arm 420. The tool assembly 430 includes a housing or tool housing 435 coupled to a proximal end of a shaft 436 and an end effector 438 coupled to a distal end of the shaft 436. The tool housing 435 can include coupling features that assist with releasably coupling the tool housing 435 to the tool driver 440 of the robotic arm 420. The tool housing 435 can include gears and/or actuators that can be actuated by the one or more motors 442 in the driver 440, as will be described in greater detail below. The gears and/or actuators in the tool housing 435 can control the operation of various features associated with the end effector 438 (e.g., clamping, firing, rotation, articulation, energy delivery, etc.), as well as control the movement of the shaft 436 (e.g., rotation of the shaft).

The shaft 436 can be fixed to the tool housing 435, or it can be releasably coupled to the tool housing 435 such that the shaft 436 can be interchangeable with other shafts. This can allow a single tool housing 435 to be adaptable to various shafts 436 having different end effectors 438. The shaft 436 can include actuators and connectors that extend along the shaft and assist with controlling the actuation and/or movement of the end effector 438 and/or shaft 436. The shaft 436 can also include one or more joints or wrists 437 that allow a part of the shaft 436 or the end effector 438 to articulate relative to the longitudinal axis of the shaft 436. This can allow for fine movements and various angulation of the end effector 438 relative to the longitudinal axis of the shaft 436. In various embodiment, the end effector can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools. For example, the end effector 438 includes first and second jaws 502, 504.

Figure 5:
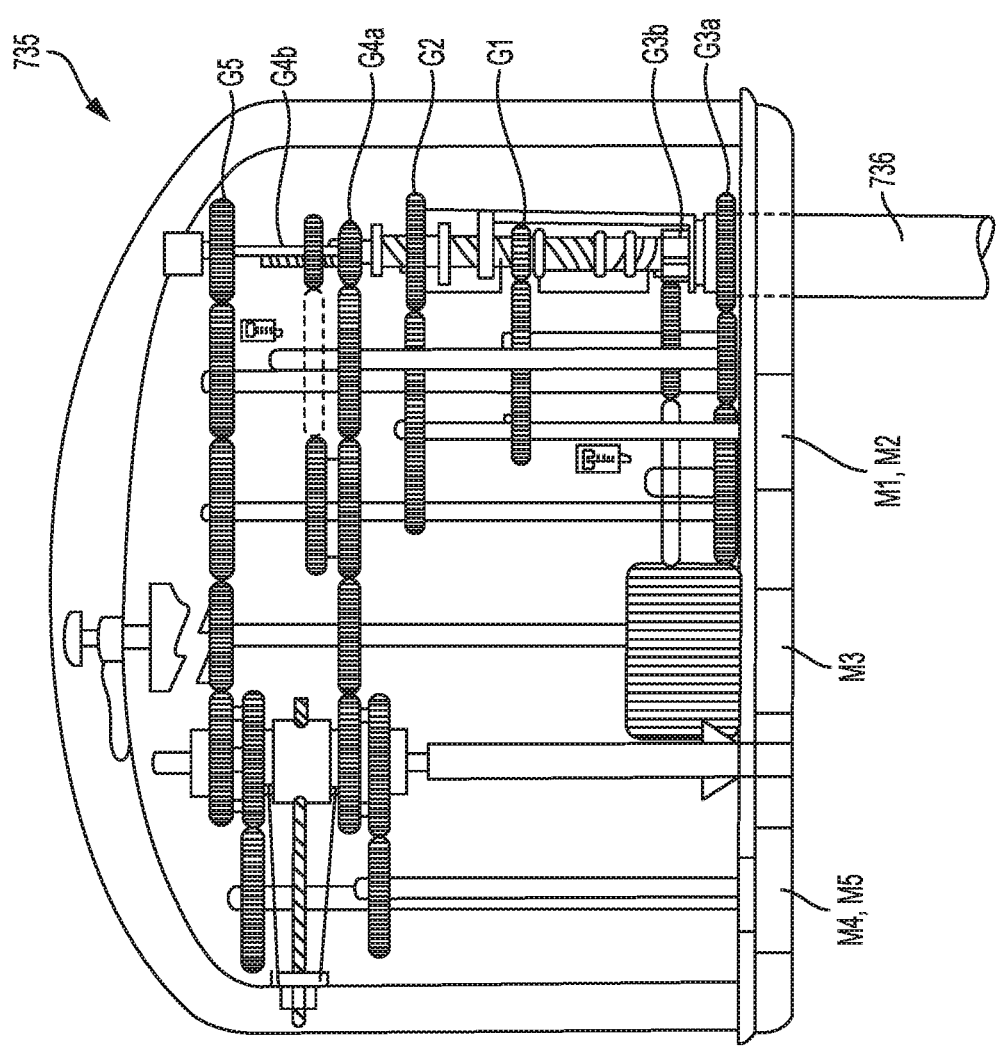
FIG. 5 is a transparent side view of an embodiment of a tool housing and a proximal end of a shaft extending from the tool housing.

FIG. 5 illustrates an embodiment of a tool housing 735 and a proximal end of a shaft 736 extending from the tool housing 735. As shown in FIG. 5, the tool housing 735 includes a plurality of actuation gears and gear shafts that can be either directly or indirectly controlled by any one of the motors 442 associated with the driver 440. For example, as shown in FIG. 5, the tool housing 735 is configured to couple to five motors at the locations indicated by reference numbers M1, M2, M3, M4, and M5. In this embodiment, tool housing 735 includes first and second articulation gears G1, G2 that are coupled respectively to the first and second motors M1, M2 via a series of one or more additional gears and shafts. Actuation of the first and second motors M1, M2 will rotate the articulation gears G1, G2, which in turn cause linear movement of an articulation cable in a proximal or distal direction to thereby cause articulation of the end effector 438 in desired left and right directions. The tool housing 735 also includes a shaft rotation gear G3a that is coupled to the third motor M3 via a series of one or more additional gears and shafts. Actuation of the third motor M3 will thus rotate the shaft rotation gear G3a thereby causing rotation of the shaft 436 of the tool assembly 430. The third motor M3 can also be configured to shift and to couple, via a series of one or more additional gears and shafts, to a head rotation gear G3b, which will cause rotation of the end effector 438 relative to the shaft 436. The tool housing 735 further includes a firm close gear G4a that is coupled to the fourth motor M4 via a series of one or more additional gears and shafts. Actuation of the fourth motor M4 will rotate the firm close gear G4a to cause linear translation of a drive screw to firmly close the jaws of the end effector 438. The tool housing 735 further includes a quick close gear G4b that can also couple to the fourth motor M4 via a series of one or more additional gears and shafts. When motor M4 is shifted into engagement with the quick close gear G4b, actuation of the fourth motor M4 will rotate the quick close gear G4b to cause linear translation of a quick close cable to quickly close the jaws of the end effector 438. Finally, the illustrated tool housing 735 includes a firing gear G5 that is coupled to the fifth motor M5 via a series of one or more additional gears and shafts. Actuation of the fifth motor M5 will rotate the firing gear G5, thereby driving a lead screw linearly to advance a sled through the end effector 438, as will be discussed in more detail below.

Figures 6, 7:
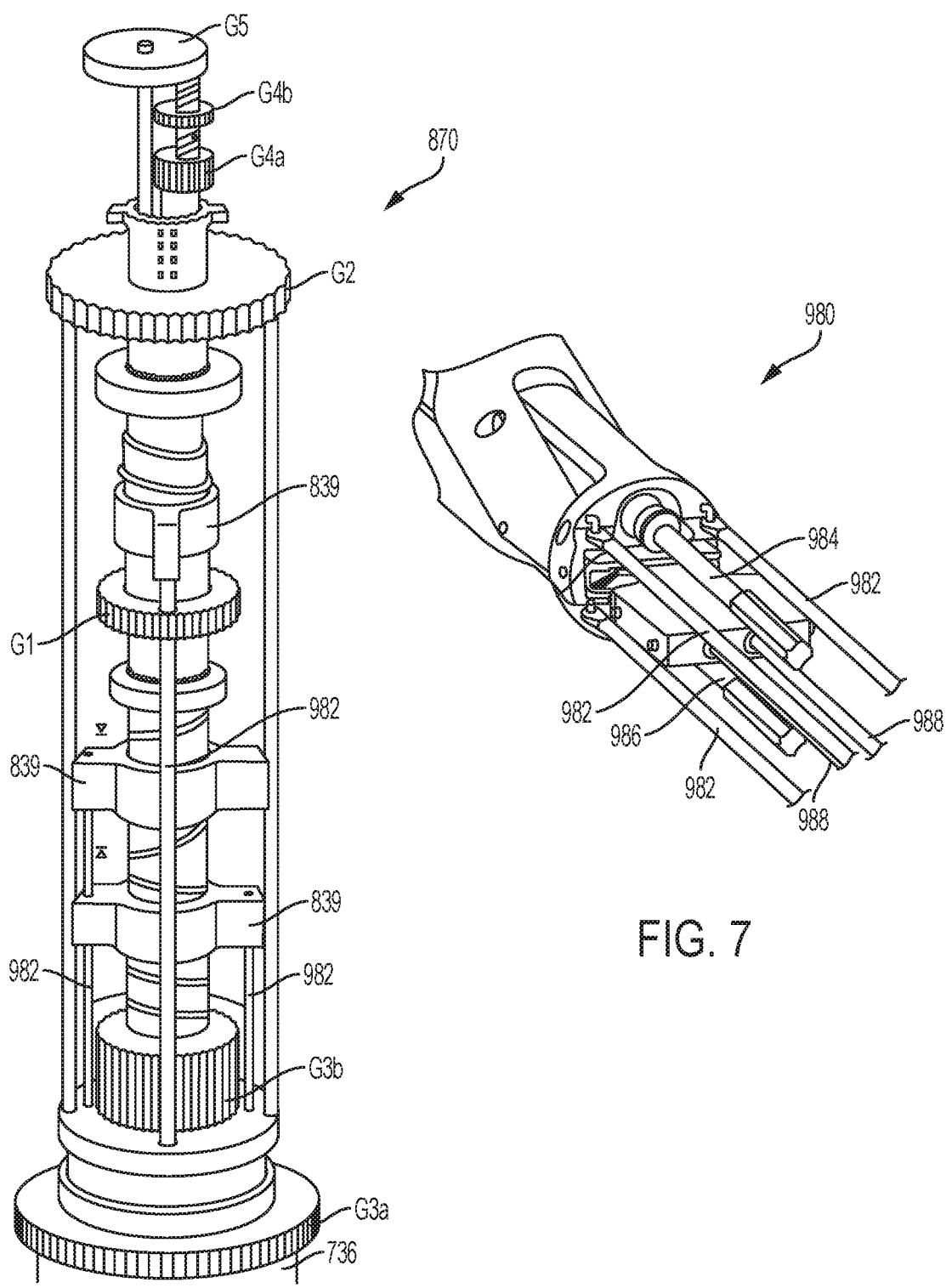
FIG. 6 is a transparent perspective view of the actuation assembly components of the tool housing of FIG. 5.
FIG. 7 is a perspective view of a distal end of the actuation shafts of a robotic surgical system having one or more features consistent with the present description.

FIG. 6 illustrates the actuation assembly 870 components of the tool housing of FIG. 5. As shown and indicated above, each of the gears G1-G5 is coupled to an actuation shaft that extends from the actuation assembly 870 and along the shaft 436 of the tool assembly 430, such as for controlling the movements of the end effector. FIG. 7 illustrates a distal end of the actuation shafts extending from a wrist 980 located just proximal of the end effector 438. The wrist 980 can allow for fine movements and angulation of the end effector 438 relative to the proximal end of the shaft 436. As shown in FIG. 7, the wrist 980 includes four articulation cables 982 that are spaced around a perimeter of the wrist 980. When actuated (e.g., pushed, pulled, rotated), the articulation cables 982 will cause articulation of the end effector 438 (e.g., movement up, down, left, right, and combinations thereof) relative to the proximal end of the shaft 436. The articulation cables 982 are connected to the articulation couplers 839, shown in FIG. 6, that are driven proximally and distally when the articulation gears G1, G2 are actuated by the first and second motors M1, M2. The wrist 980 also includes an upper rotary driver 984 that when actuated can cause the pair of jaws of the end effector 438 to firmly close. The upper rotary driver 984 is coupled to the firm close gear G4a shown in FIG. 6 such that rotation of the firm close gear G4a by the motor M4 causes rotation of the rotary driver 984. The wrist 980 can also include a lower rotary driver 986 that when actuated can cause movement of a sled located at the end effector 438. The lower rotary driver 986 is coupled to the firing gear G5 shown in FIG. 6 and it likewise rotates in response to rotation of the firing gear G5. The illustrated wrist 980 further includes a linear pull cable 988 that is coupled to the quick close gear G4*b* shown in FIG. 6 and that moves linearly in a proximal direction to cause rapid close of the pair of jaws.

Figure 8:
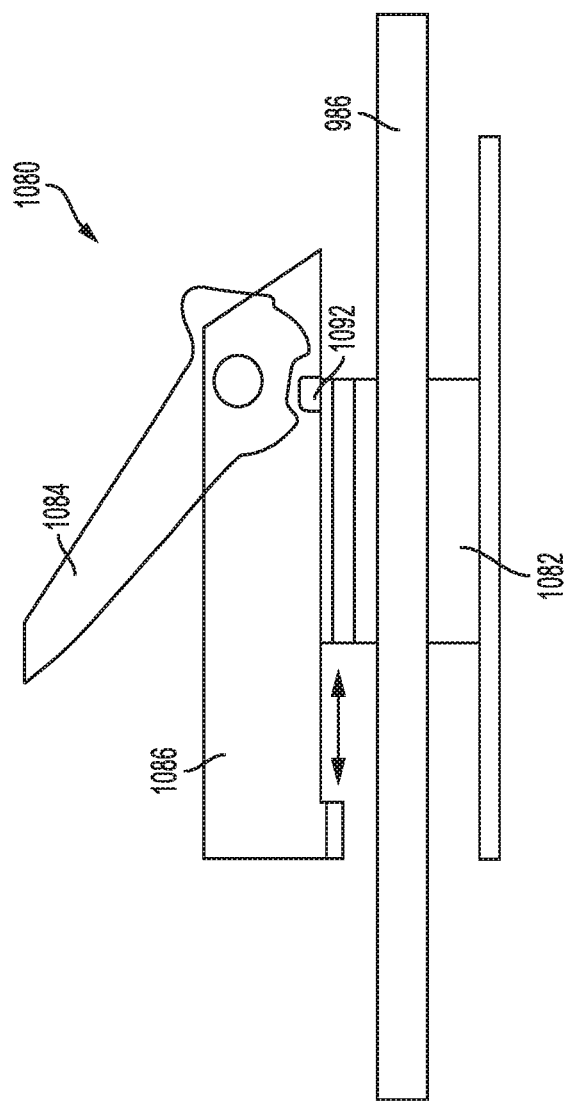
FIG. 8 is a side view of a portion of an exemplary end effector for use with a robotic surgical system having one or more features consistent with the present description.

FIG. 8 illustrates a portion of an end effector 1038 having a knife actuation assembly 1080 that includes a drive member 1082, a knife 1084, a knife sled 1086, and a lead screw or rotary driver 986. The drive member 1082 includes internal threads that are threadably coupled with the rotary driver 986. Such coupling can allow drive member 1082 to move along the rotary driver 986 when the rotary driver 986 is rotated. As discussed above, the rotary driver 986 can be actuated at the wrist 980, as shown in FIG. 7, thereby causing rotation of the rotary driver 986 and linear movement of the knife sled 1086 along the rotary driver 986. The rotary driver 986 is coupled to the firing gear G5 shown in FIG. 6. The knife actuation assembly 1080 is configured to orient the knife 1084 in a cutting position when the drive member 1082 pushes the knife sled 1086 along the rotary driver 986 and to stow the knife 1084 when the drive member 1082 is moved proximally relative to the knife sled 1086. In operation, the rotary driver 986 is first rotated to advance the drive member 1082 distally along the rotary driver 986 thereby pushing the knife sled 1086 in the distal direction and angularly orienting the knife 1084 in the cutting position. At the end of the distal movement of the assembly 1080, the direction of rotation of the rotary driver 986 is reversed to retract the drive member 1082 proximally relative to the knife sled 1086, thereby causing the knife 1084 to rotate down into the stowed position, such as via interaction between an interface feature 1092 and the knife 1084.

A robotic surgical system consistent with the present description can incorporate a camera and an associated viewing field to allow the robotic surgical system to provide any feedback to corresponding end effectors. For example, the robotic surgical system can include an end effector over which the system can have control. The system can provide instructions to the end effector in the form of a declared action (e.g. firing, speed of cutting element, clamping speed, etc.). Under ideal surgical conditions, the end effector proceeds with performing the declared action as instructed based on user input instructions. However, under many surgical conditions, the end effector might not be able to perform the declared action as instructed for a variety of reasons, such as overly thick tissue, unexpected surgical conditions, human error, etc. The camera can be used to visually detect at least one visual indicator on the tool, on adjacent tools, and/or on tissue. For example, a visual indicator indicative of a length scale can allow an action of the tool to be visually measured by the camera and transmitted to a corresponding control system, such as the control system 315 described above. The robotic system can modify the action of the tool based on the visually measured action.

Figure 9:
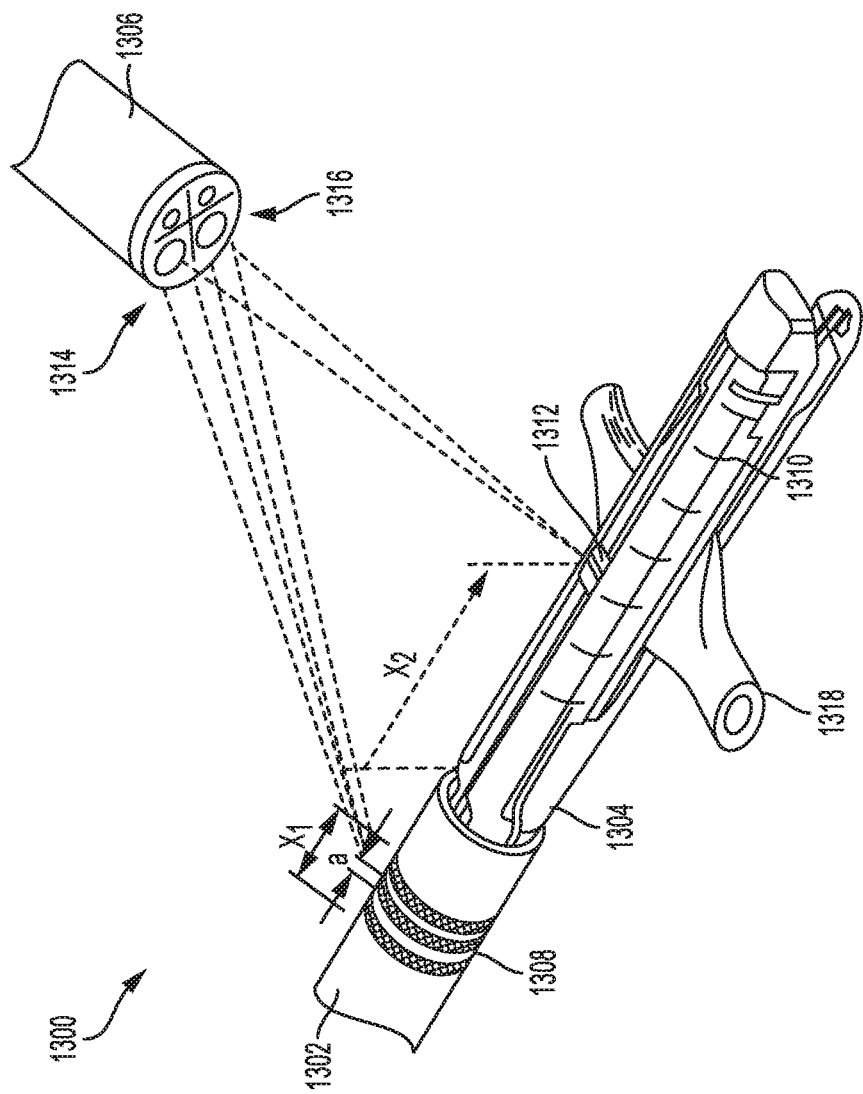
FIG. 9 is a perspective view of a portion of a robotic surgical system having one or more features consistent with the present description.
Figure 10:
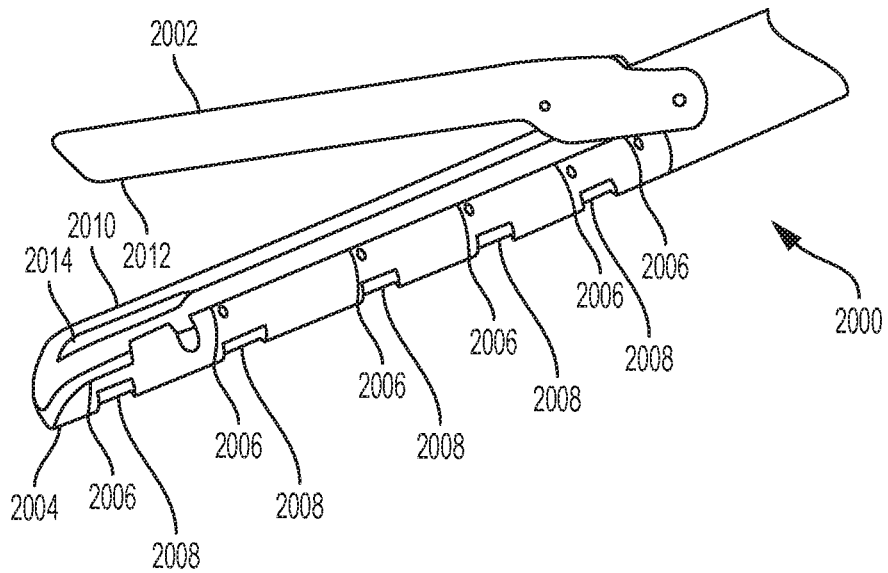
FIG. 10 is a perspective view of an embodiment of an end effector consistent with the present description.
Figure 11:
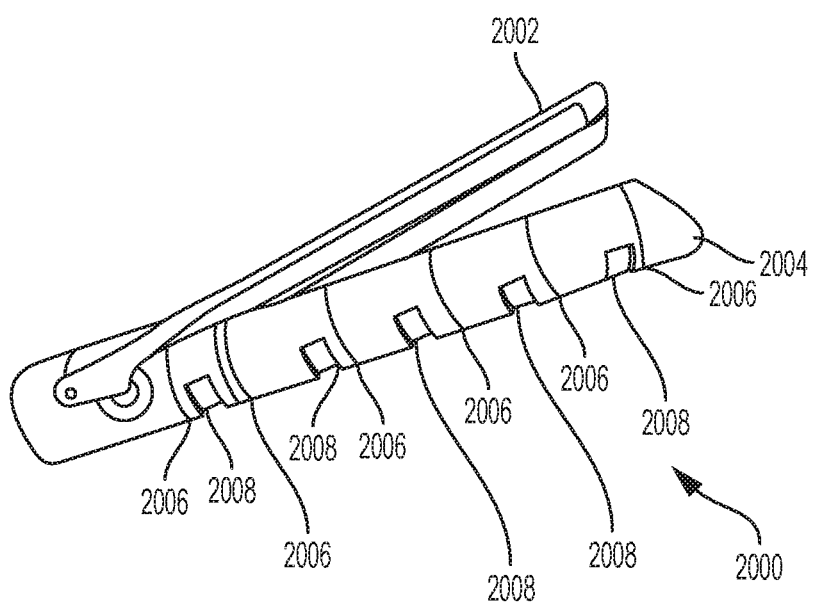
FIG. 11 is another perspective view of the end effector of FIG. 10.
Figure 12:
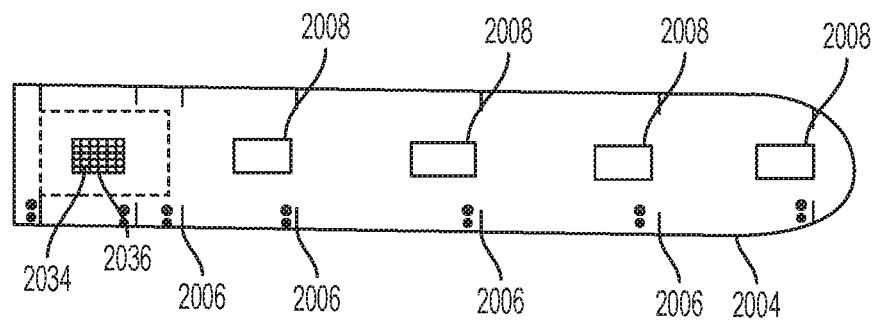
FIG. 12 is a bottom view of the end effector of FIG. 10.
Figure 13:
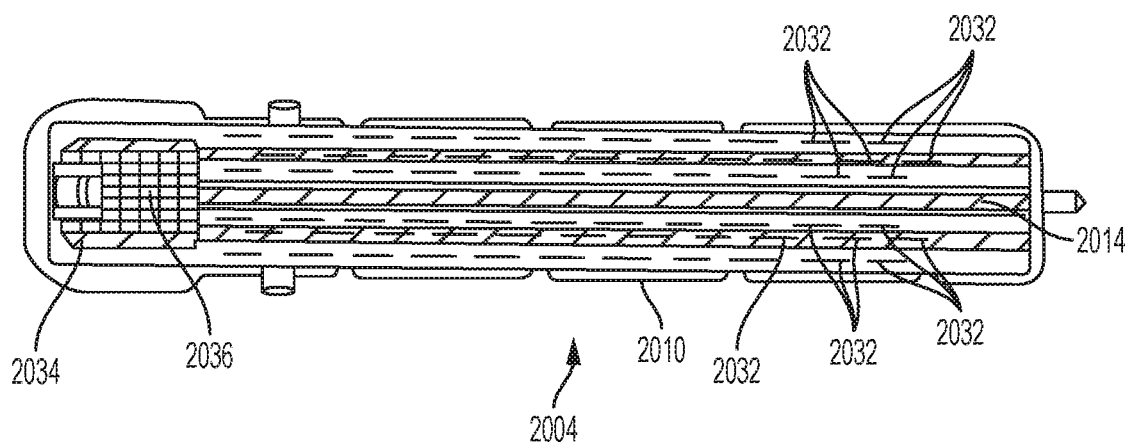
FIG. 13 is a top view of a surface of a jaw of the end effector of FIG. 10.

FIG. 9 illustrates one embodiment of a portion of a robotic surgical system consistent with the present description. As illustrated in FIG. 9, a portion of a robotic surgical system 1300 includes a tool having a tool shaft 1302 with an end effector 1304 coupled to a distal end of the tool shaft 1302. A scope, such as a binocular scope 1306, can be used to view the tool shaft 1302 and the end effector 1304. The tool shaft 1302 can include one or more fixed-size and fixed-space indicators in the form of markers 1308 and the end effector 1304 can also include one or more fixed-size and fixed-space markers 1310. In the example illustrated in FIG. 9, the end effector 1304 can include a cutting element or sled, as described above, having a marker 1312 thereon.

The scope 1306 can include imaging systems, such as cameras 1314 and 1316. Imaging systems provided herein can include one or more devices primarily used to capture visual data, such as cameras, and can also include one or more devices used to capture non-visual image data, such as IR, UV, or X-Ray, in which data is captured and then transformed to provide visual information. Each camera can obtain a separate image of the tool shaft 1302 and its markers 1308, the end effector 1304 and its markers 1310, and the sled and its marker 1312. Markers 1308, 1310 can have a fixed spacing. Each marking within the set of markers 1308 can have a fixed width a, and the entire set of markers 1308 can have an overall fixed width $X_1$. Furthermore, the end effector 1304 can have a known length and width. Because the lengths and widths are fixed and known, the markers 1308, 1310 can be used to determine a coordinate system with a length scale and a relative position of the shaft 1302 and the tool 1304 to the scope 1306. For example, the images of the tool shaft marker 1308 and the surgical tool marker 1310 can be used to determine the location of the surgical tool 1304 relative to the binocular scope 1306, for example through projective reconstruction. Images of the sled marker 1312 can also be used to determine the location of the sled along the length of the end effector 1304, for example through projective reconstruction. A distance $X_2$ representing the distance that the sled has traveled can be determined by the comparison of the sled marker 1312.

The sled marker 1312 position relative to the end effector 1310 and/or the shaft markings 1308 can also be detected and compared to the declared action of the sled based on a user input. As described above, the system 1300 using the cameras 1314, 1316 can determine the coordinate system and scale based on one or more of the markers 1308, 1310, can determine the location of the end effector 1302, and can determine the location of the sled based on the sled marker 1312 when the tissue 1318 is grasped. Based on the declared action of the sled, i.e. the instructions input into the system by a user, the robotic surgical system 1300 can determine where the sled should be at any moment based on a variety of factors, such as an amount of power supplied to the system 1300 to advance the sled and/or a declared speed of the sled. Using the scope 1306 and the sled marker 1312, the system 1300 can determine the actual position and/or speed of the sled at any point in time during firing. By comparing the declared position and/or speed of the sled and the actual position and/or speed of the sled, the system 1300 can determine if the sled is in its declared position and/or speed, in which case the system 1300 can take no action. Or if the sled is not at its declared position and/or speed, the system can alter the actuation of the sled. For example, if the sled is moving slower than expected, the system can surmise that the tissue 1308 grasped by the tool 1304 is thicker than expected and can slow down the sled to ensure a clean cut of the tissue 1308. In another example, if a declared action is to accelerate the sled but the system 1300 detects that the knife blade is approaching the distal end of the tool 1304 and thus runs a risk of colliding with the distal end of the end effector 1304, the system 1300 can reduce the speed of the sled to ensure no collision and/or damage occurs. Through this feedback and exchange in the robotic surgical system 1300, actuation of the end effector 1304 can be modified based on the visually measured action occurring during an operation, thus allowing the system to react appropriately to what is actually happening and encountered during an operation rather than proceeding with what was expected to be found without regards to the actual situation. While a binocular scope is illustrated herein, a scope using any number of imaging systems including any number of cameras can be used in any of the embodiments provided herein.

While line markers are illustrated in FIG. 9, a variety of different visual indicators can be used. In various embodiments, a scale and/or ruler can be placed on an end effector, components thereof, and/or a shaft to indicate a scale of an operation site so that a camera can use the scale to measure sizes and/or distances of the end effector, components thereof, and/or shaft, and can measure a position and/or distance of the end effector and/or shaft with regard to other tools and/or surrounding tissue. The scales and/or rulers placed on the tools can take a variety of forms. For example, the indicator can be a grid pattern(s), band(s), particulate on tissue, etc. Grid patterns can be placed anywhere on a tool, such as the shaft, the end effector, a sled, or any moving part, etc. The grid pattern can be of a known configuration so that the camera can take an image of the grid pattern and the control system can be able to apply an appropriate scale to the operation site based on spacing and/or orientation of the grid pattern. The grid pattern, bands, or other markings can be placed anywhere on a tool and can also have a known pattern and/or spacing and/or width to allow the control system to determine an appropriate scale based on any images obtained by the camera. In other embodiments, a plurality of cameras can be used, and the coordinate system can be reconstructed. In other aspects, a particulate can be applied to tissue surrounding the operation site. Once the particulate is applied, the camera(s) can initially image the site and the control system can determine relative positioning and/or motion based on any changes to locations of particulate from subsequent imaging of the site, looking at various factors such as strain and/or position of the tissue relative to various tool devices and in relation to a visual indicator that provides a length scale.

In some embodiments multiple visual indicators are used to allow at least one indicator to always be within camera view during any operation. FIGS. 10-13 illustrate one embodiment of an end effector 2000 with multiple visual indicators. The end effector 2000 can operate with a robotic surgical system as described herein that includes a scope with at least one camera. As illustrated, the end effector 2000 includes a first jaw 2002 and a second jaw 2004. The first jaw 2002 is in the form of an anvil and has a tissue grasping surface 2012 with pockets (not shown) for forming staples. The second jaw 2004 includes a cartridge carrying staples, and it has a tissue grasping surface 2010 with a slot 2014 running longitudinally therethrough and approximately parallel to a central axis of the end effector 2000. The second jaw 2004 has an inner lumen or channel extending longitudinally therethrough that is configured to receive a sled 2034, partially visible in FIGS. 12 and 13. The sled 2034 is advanceable through the second jaw 2004 from a proximal end to a distal end of the end effector 2000. As the sled 2034 is advanced through the second jaw 2004, tissue grasped between the first and second jaws 2002, 2004 is cut by a cutting element on the sled that advances through the channel 2014. Staples are fired from the cartridge through a plurality of slots 2032 and through the cut tissue on either side of the channel 2014 such that tissue is sealed as it is cut by the advancing sled 2034.

As indicated above, the end effector can include one or more visual indicators for indicating a position/location and/or length scale of the end effector or components thereof. In the illustrated embodiment, the end effector 2000 includes multiple visual indicators. The end effector 2000 has a first visual indicator in the form of a plurality of length markings 2006 spaced on the second jaw 2004, a second visual indicator in the form of a plurality of openings 2008 formed in and spaced along the second jaw 2004, and a third visual indicator in the form of a grid 2036 disposed on a distal bottom surface of the sled 2034.

Length markings 2006 are configured to provide a visual indication of a length scale of the second jaw 504. By using the length markings 2006, the surgical system disclosed herein can calculate a distance between two points on the end effector 2000. The illustrated length markings 2006 extend at evenly spaced intervals along the second jaw 2004 from the proximal end to the distal end of the end effector 2000, and will visually indicate a length of the end effector 2000 and/or a travel distance of the sled 2034. For example, the system can use the calculated distance to determine a speed of travel of the sled 2034. The system can thereby adjust, i.e. increase or decrease, the speed as may be desired. For example, the illustrated jaw has markings that correspond to the numbers 10, 20, 30, and 40, as well as the term "cut." The "30" marking, for example, will indicate that there is 30 mm more before a complete cut is made. The first and second "cut" markings will indicate that cutting of the tissue occurs between those two markings. Because the illustrated markings 506 have a predetermined spacing, the surgical system described herein can be programmed to correlate to the visual indicator. The system can view the markings 2006 through one or more cameras to determine an approximate length of the end effector 2000 and apply a corresponding length scale. While the markings 2006 herein are represented by lines, numbers, and words, as discussed above any visual means of indicating length and/or scale can be used, such as notches, dashes, words, etc.

The openings enable viewing of the sled 2034, and in general enable viewing at multiple positions during advancement of the sled 2034 along the second jaw 2004. In the illustrated embodiment, the openings 2008 are square cut openings in the second jaw 2004. The openings 2008 extend into the inner cavity of the second jaw 2004 and are configured to allow the sled 2034 to be visible therethrough as the sled 2034 is advanced distally through the end effector 2000. In various embodiments, numerous styles and shapes of openings can be used as long as a sled is visible through the openings, for example circles, ovals, cuts, etc. The openings 2008 are evenly spaced along a surface of the second jaw 2004 that is opposite to the tissue engaging surface 2010. In other embodiments, the location of the openings can vary. For example, the openings can be disposed along one or both sides of the second jaw, as long as a structural integrity of the jaw is maintained. Varying numbers of openings can be used, such as 2, 3, 4, 5, etc. The system can use one or more cameras to view the location of the sled 2034 as it passes through a single opening or across multiple openings at a select time and/or over a period of time to determine a speed of the sled 2034. As with the embodiment in FIG. 9, the system can compare a declared position and/or speed of the sled 2034 based on instructions input by a user to an actual position and/or speed of the sled 2034 determined by use of the camera(s) and the control system. If the actual position and/or speed does not match the declared position and/or speed, the system can adjust a speed of the sled 2034 (including stopping the sled 2034) based on desired conditions. For example, if thick tissue is encountered, the sled 2034 might advance slower than declared by the user input, at which point the system can reduce a speed of the sled 2034 to ensure a clean cut of any tissue.

As indicated above, the grid 2036 disposed on the distal bottom surface of the sled 2034 is visible through the openings 2008 as the sled 2034 is advanced distally through the end effector 2000. The grid 2036 can be used in coordination with the openings 2008 by the system to allow the system to determine the actual speed and/or position of the sled 2034 as described above by allowing the system to track a location of the grid 2036 (and subsequently a location of the sled 2034), either between openings or with respect to a time it takes the grid 2036 to pass across one opening. However the grid 2036 can also be used independently to provide a scale and/or a position of the sled 2034 because the grid 2036 can have lines with fixed and known spacing and/or width and/or orientations. By analyzing any images of the grid 2036, the system can make determinations similar to those of the markings 2008 representing the first visual indicator, especially regarding a length scale. While a grid is illustrated, as noted above a variety of visual indicators can be used, such as visually distinct markings having known patterns.

As the sled 2034 is advanced through the end effector 2000, the control system can calculate a variety of factors regarding the sled 2034 depending on a desired outcome, such as the position, the distance traveled, and the traveling speed. A variety of control mechanisms and feedback controls can be performed by the control system, such as slowing an advance of the sled 2034 as the sled 2034 approaches the distal end of the end effector 2000 or ending a firing stroke to prevent the sled 2034 from colliding with any tissue or the distal end of the end effector 2000. The control system can also increase or decrease a traveling speed of the sled 2034 if the traveling speed is less than or greater than a threshold value set by a user and/or the control system. For example, if thick tissue is encountered and a slower speed is desired to ensure a clean cut and clean staple firing, the speed of the sled 530 can be slowed by the system. The traveling speed of the sled 2034 can also be monitored to ensure a temperature of the sled 2034 does not exceed some pre-determined threshold, which may cause damage to surrounding tissue and/or the end effector 2000. As discussed in more detail above, the system can also perform a feedback loop of determining an actual position and/or speed of the sled 2034 based on the first, second, and/or third visual indicators and comparing the determined actual position and/or speed to a declared position and/or speed based on a declared user input. If the actual position and/or speed does not match a declared speed and/or position of the sled 2034, the control system can vary the speed of the sled 2034 to correct for encountered conditions. For example, if the control system detects that the sled 2034 is moving slower than expected, the control system can assume a presence of thicker tissue and take an appropriate response, such as slowing the speed of the sled 2034 to ensure a smooth cut. Control can be exercised over the sled 2034 by use of a variety of control algorithms, and a position of the sled 2034 can be displayed on a display screen, such as an LCD screen, through various software approaches.

Control algorithms and displays are not limited to control over a sled and/or displaying a location of the sled. One or more control algorithms and one or more displays can be used to control one or more tool actuations, such as clamping, articulation, rotation, etc. Any of the articulations and functions discussed herein can be controlled through control algorithms and can be displayed on one or more display screen, such as LCD screens, through various software approaches. Additional measurements and/or estimations can also be made based on visual indicators, such as an angle between two jaws on an end effector. As with the embodiments described herein, a jaw angle and/or distance between distal tips of jaws on an end effector can be measured using the visual indicators described herein. A declared position and/or angle of jaws of an end effector can be compared to an actual position and/or angle to provide feedback regarding encountered operating conditions. For example, if jaws closing on tissue are closing slower than expected, a system can determine that any tissue grasped therein might be thicker than expected.

Figure 14:
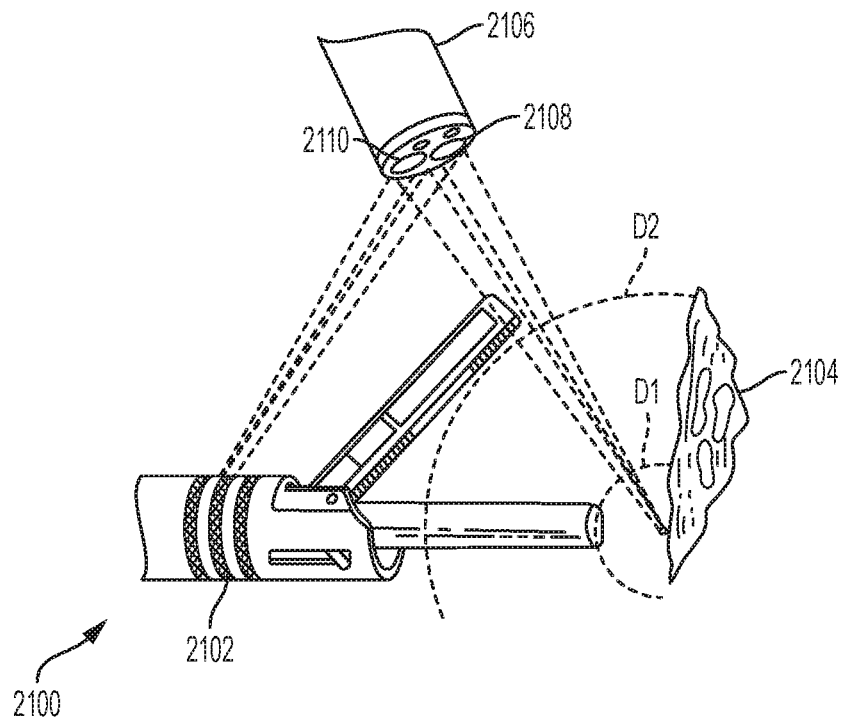
FIG. 14 is a perspective view of a portion of a tool assembly and a camera for use with a robotic surgical system having one or more features consistent with the present description.
Figure 15:
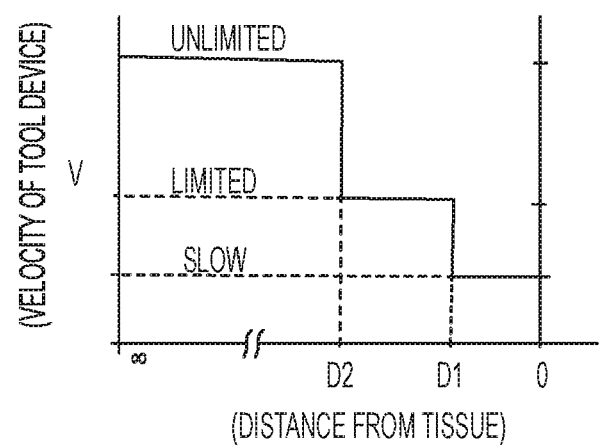
FIG. 15 is a graphical depiction of velocity changes over time as the tool assembly of FIG. 14 moves toward tissue.

While the above embodiments provide control over various moving components within an end effector, a robotic control system can also serve to control and/or limit movement of a tool and an end effector within a body cavity based on visual indicators. FIG. 14 illustrates an end effector 2100 with visual indicators in the form of markings 2102 similar to the embodiment of FIG. 9. A binocular scope 2106 is positioned with cameras 2110, 2108 positioned to view the markings 2102 and a tissue 2104 of a patient. As with the above embodiments, the markings 2102 can provide a scale to a robotic control system controlling the end effector 2100. As the end effector 2100 approaches the tissue 2104, the system can control the speed of the end effector 2100 based on its distance from the tissue 2104. As illustrated in FIG. 15, when the end effector 2100 is far away from the tissue 2104, the user input speed and/or velocity of the end effector 2100 is not limited by the system based on proximity to the tissue. As the end effector 2100 gets closer to the tissue 2104, for example within a proximity zone $D_2$, the speed and/or velocity is limited. As the end effector 2100 gets even closer to the tissue, for example within a proximity zone $D_1$ such that the end effector 2100 is almost contacting the tissue, the speed and/or velocity is slowed further. A system can therefore set a maximum speed and/or velocity of an end effector and/or various tool devices based on a proximity of the end effector and/or various tool devices to other structures in a body of a patient during operation. This can help ensure that no accidental collisions occur between tools and tissue, which can cause damage to the tools and harm to the tissue of a patient. While a binocular scope is illustrated herein, a scope using any number of imaging systems including any number of cameras can be used.

Figure 16:
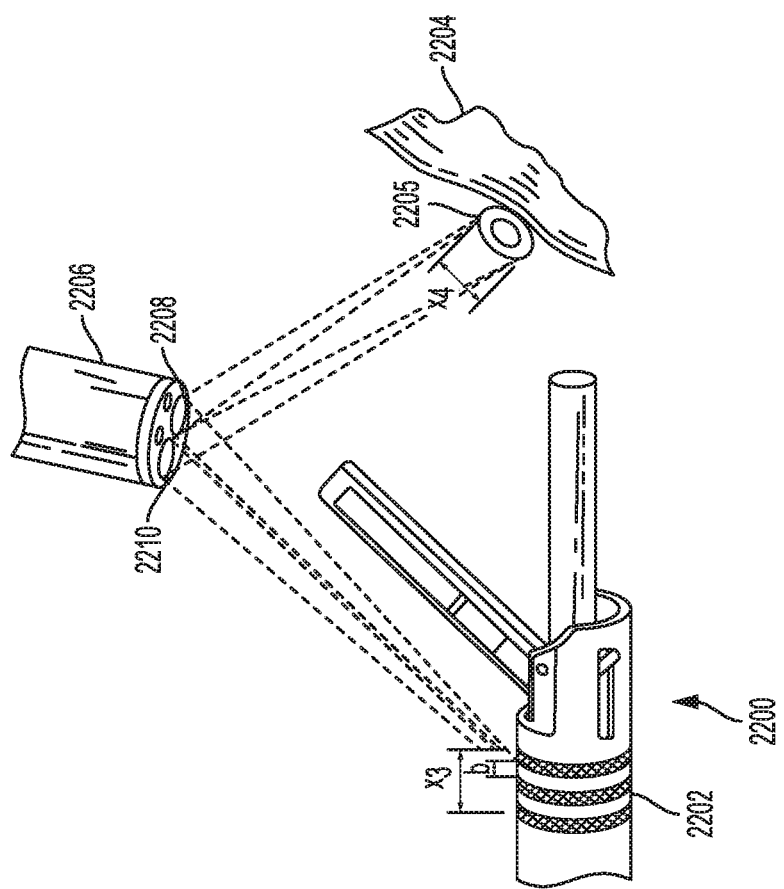
FIG. 16 is a perspective view of a portion of a tool assembly and a camera for use with a robotic surgical system having one or more features consistent with the present description and tissue.

Visual indicators can also be used by a robotic surgical system to estimate dimensions within an operation site. FIG. 16 illustrates an end effector 2200 with visual indicators in the form of markings 2202 similar to the embodiments of FIG. 9 and FIG. 14. A binocular scope 2206 is positioned with cameras 2210, 2208 positioned to view the markings 2202 and a tissue 2204 of a patient. As with the above embodiments, the markings 2202 can provide a scale to a robotic control system controlling the end effector 2200. As with the embodiment of FIG. 9, each mark in the markings 2202 can have a fixed width b, and the markings 2202 can have an overall fixed width $X_3$. Because the lengths and widths are fixed and known, the system can use the binocular scope 2206 with the two cameras 2210, 2208 to compare and contrast the markings 2202 with a blood vessel 2205 against the tissue 2204. The dual focal length of the scope 2206 can allow the system to estimate a size $X_4$ of the vessel 2205 based on the markings 2202. This estimation can provide feedback to the system and/or a user to consider the appropriateness of the size of the current end effector being used. For example, the estimated size can confirm using a current end effector and/or current settings on an end effector or can cause a user to adjust an end effector and/or settings on the end effector, for example adjusting a level of energy delivery to the estimated vessel 2205. For any visual indicators, a length scale is required to estimate any actual dimensions, distances, and/or lengths of tools and surrounding tissue, while visual indicators can provide relative positions without a length scale. While a binocular scope is illustrated herein, a scope using any number of imaging systems including any number of cameras can be used.

In each embodiment discussed herein, a visual indicator, such as a marker, can be disposed on tissue directly when various tools rely on knowing a position of the tissue. The marker on tissue can allow a robotic system to determine a location and/or position of the tissue independently and/or in relation to tools that are part of the system.

There are additional ways in which measurements can be determined, for example by various sensors known in the art. If another means of measuring is used at an operating site, visual indicators can still be used to provide a secondary and/or redundant measurement and be compared to the other sensed measurements to serve as a safety mechanism and to provide useful feedback to any robotic surgical system.

Figure 17:
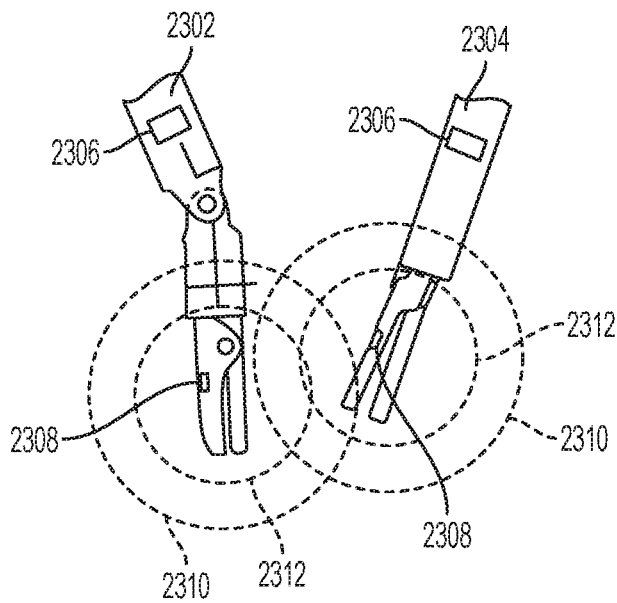
FIG. 17 is a side view of a portion of two tool assemblies for use with a robotic surgical system having one or more features consistent with the present description.

Robotic surgical systems can also use a variety of methods, devices, and systems to prevent more than one tool within a robotic system from colliding or crashing into each other. The tools can be end effectors and/or other devices within the body that are not part of any robotic surgical system, such as a retractor. FIG. 17 is an illustration of a portion of two tools 2302, 2304 that are part of a robotic surgical system, having one or more features consistent with the present description. The robotic surgical system can be configured to adjust threshold velocities of either a tool advancement due to the tool driver or the actuation of the tool itself due to the proximity of another tool location or speed. Control of the tools 2302 and tools 2304 can be performed by a master control system, such as control system 315, a secondary controller 2306 disposed in one or more components of the robotic surgical system, or the like. As used herein, the term "controller" can be used to refer to the master control system 315, a secondary controller 2306, and/or another controller. The controller can be configured to control one or more articulation joints, rotational joints, or the like, of the robotic system.

The controller can be configured to retard the motion of the tools 2302 and 2304 toward each other or other elements within the surgical area, provide an alert based on the proximity of an end effector of one of the tools 2302, 2304 with another tool or element within the surgical area.

Figure 18:
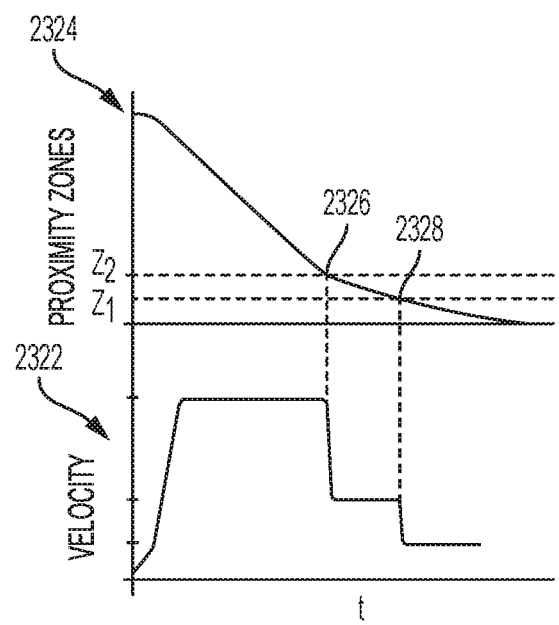
FIG. 18 is a graphical depiction of velocity changes over time as the tool assemblies of FIG. 17 move toward each other.

FIG. 17 shows two proximity zones, a general proximity zone 2310 and a close proximity zone 2312 for each of the tools 2302, 2304. The presently described subject matter contemplates any number of zones, or a gradated zone from an outer perimeter inward to the tool 2302, 2304. The controller can be configured to limit the velocity of the tool assemblies operating within the general proximity zone 2310 or the close proximity zone 2312. FIG. 18 includes a graph 2322 illustrating the velocity of the tools 2302, 2304, as they move from outside of the general proximity zone, enter the general proximity zone at 2326, pass through the general proximity zone, enter the close proximity zone at 2328, and pass through the close proximity zone. FIG. 18 also includes a graph 2324 illustrating the movement over time as the tools move closer together. Graph 2322 is a representation showing the maximum velocities of the tools at each of the different zones.

Each tool 2302, 2304 can include a sensor 2308. The sensor 2308 can be configured to facilitate a determination by a controller, such as controller 2306, of the location of one or more of the tools 2302, 2304. Multiple sensors 2308 can be used and disposed at various locations along the length of the robot arms. In one embodiment, the sensor 2308 can be a six-axis sensor. A six-axis sensor can include a multi-axis accelerometer, a multi-axis magnetic sensor, or the like. The sensor 2308 can be configured to detect motion of the tools 2302, 2304 and continually transmit motion information back to a controller. The initial location of the tools 2302, 2304 can be known with respect to a fixed point within the operating room in which a robotic surgical system, such as the robotic surgical system 300, is installed, or with respect to other tools of the robotic surgical system. The motion information transmitted by the sensor 2308 can be represented geometrically, either by one or more components of the sensor 2308, or by the controller. The controller can continually track the motion information of the tools 2302, 2304, to know the location of each tool 2302, 2304 relative to the initial location of the tool 2302, 2304. Knowing the location of a tool relative to an initial location can facilitate collision avoidance even when the tools are outside of the field of vision of a camera or other video sensor.

By tracking the motion of the tools 2302, 2304, the controller can be configured to determine when one tool assembly, for example, tool 2302, is within a general proximity zone of another tool assembly, for example, tool 2304, or another object having a known location. When the tool 2302 comes within a general proximity zone of another tool assembly or object, the controller can be configured to reduce the velocity of the tool 2302 to a general proximity velocity, as illustrated in FIG. 18. When the tool 2302 is within a close proximity zone of another tool or object, the controller can be configured to reduce the velocity of the tool 2302 to a close proximity velocity. In some variations, the controller can be configured to stop the movement of the tool 2302 in response to a determination that the tool 2302 is within a threshold distance of another tool or object. In other variations, the controller can be configured to reduce the velocity of the tool 2302 to a collision velocity. The collision velocity can be a velocity at which collisions would not cause damage to the tool(s), other object(s), or the tissue of the patient. Upon a detection that the tool 2302 has collided with another tool, object, or patient tissue, the controller can be configured to stop the motion of the tool. A person skilled in the art will appreciate that the motion of the tool is controlled by the robotic arm coupled thereto.

Figure 19:
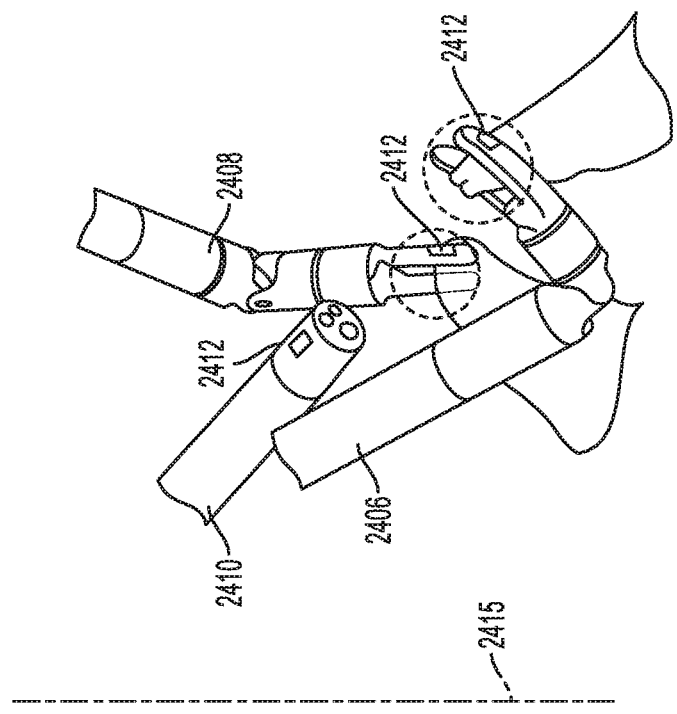
FIG. 19 is a perspective view of a magnetic transmitter for use with a robotic surgical system having one or more features consistent with the present description and tool assemblies and a binocular scope operating within a magnetic field of the magnetic transmitter.
Figure 19:
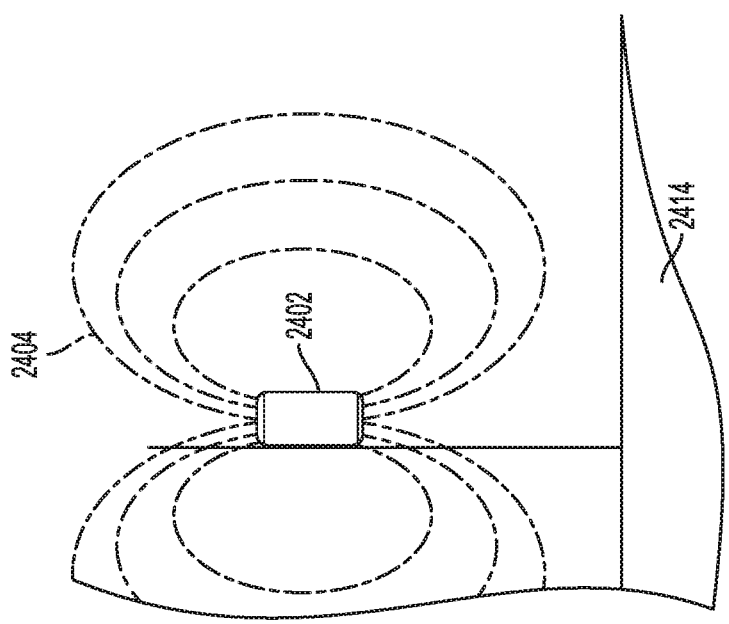

FIG. 19 is an illustration of a magnetic transmitter 402 for use with a robotic surgical system, having one or more features consistent with the present description. One or more magnetic transmitters 1402 can be disposed in the vicinity of the robotic surgical system and can have a known location relative to the robotic surgical system. The magnetic transmitter(s) 1402 can be configured to generate a magnetic field 1404. The magnetic transmitter(s) 1402 can each be configured to modulate their emitted magnetic field 1404 differently. This will allow magnetic field sensors to detect which magnetic field they are detecting or may be able to detect the effects of multiple different magnetic fields simultaneously. Modulating the emitted magnetic field 1404 in such a way that frequency discrimination and quadrature detection can be one example of enabling the detection of multiple different magnetic fields simultaneously.

FIG. 19 also illustrates tools 2406 and 2408 and a binocular scope 2410 operating within a magnetic field 2404 within a body of a patient and separated from an exterior of the patient (illustrated by a broken line 2415 in FIG. 19). The first tool 2406, second tool 2408, and binocular scope 2410 can each include a magnetic field sensor 2412. The magnetic field sensors 2408 can each be a six-axis sensor which may include magnetic field sensors. The magnetic field sensors 2412 will be effected by the magnetic field 2404 generated by the magnetic field generator 2402 disposed at a known location proximate to the robotic surgical system.

A controller, such as the master control system 315, or the like, can be configured to receive magnetic field information from the magnetic field sensors 2412 and determine the location of the tools 2406, 2408 and binocular scope 2410 based on the magnetic field information. The location of the tools 2406, 2408 and binocular scope 2410 can be determined relative to a fixed point within an operating room or the location can be determined relative to each other. In some variations, the fixed point can be a fixed point within the bed 2414 on which the patient is lying.

The controller can be configured to monitor the location of the tools 2406, 2408 and binocular scope 2410 relative to a fixed point and/or each other and reduce the velocities with which the tools 2406, 2408 and binocular scope 2410 move toward each other when the tools 2406, 2408 and binocular scope 2410 move within close proximity of each other. While a binocular scope is illustrated herein, a scope using any number of imaging systems including any number of cameras can be used.

Figure 20:
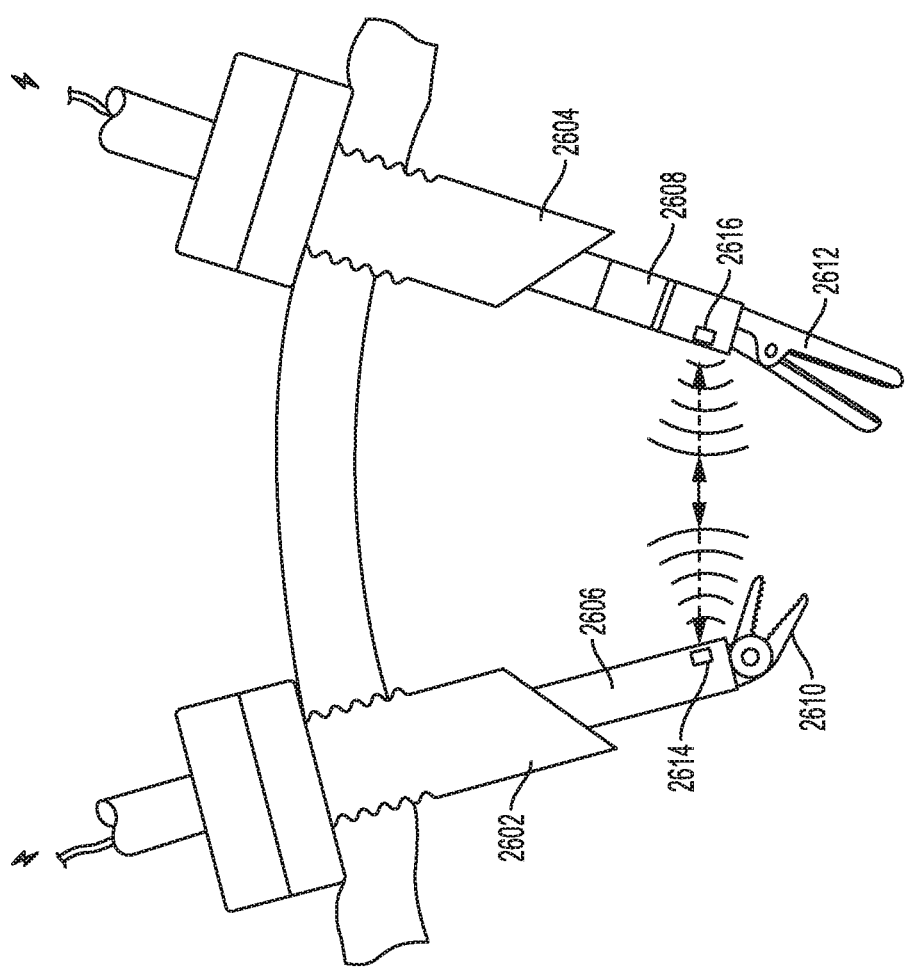
FIG. 20 is a side view of surgical tools for use with a robotic surgical system having one or more elements consistent with the described subject matter.

FIG. 20 illustrates another embodiment of surgical tools for use with a robotic surgical system. The robotic surgical system can include a first tool shaft 2602 and a second tool shaft 2604. The tool shafts 2602, 2604 can have end effectors 2606, 2608 coupled to a distal end thereof. In the illustrated embodiment, each end effector includes a pair of jaws 2610, 2612.

One or more motion sensors 2614 can be disposed on the first end effector 2606 and one or more motion sensors 2616 can be disposed on the second end effector 2608. The one or more motion sensors 2614, 2616 can be configured to transmit and receive proximity signals. For example, the motion sensor(s) 2614 can emit a proximity signal. The motion sensor(s) 2616 on, or near, the second end effector 2608 can be detect the strength of the proximity signal emitted by the motion sensor(s) 2614 on, or near, the first end effector 2606, and vice versa. The strength of the signals can be used to determine the relative distance between the two end effectors 2606, 2608. A controller can be configured to reduce the velocity of the motion of the end effectors 2606, 2608 toward each other when the controller determines that the end effectors 2606, 2608 are within a threshold distance of each other.

In some variations, the controller can be a master control system such as control system 315, one or more secondary controllers in one or more components downstream from the master control system 315, and/or a controller disposed within the end effectors 2606, 2608. The controller within the end effectors 2606, 2608 can be configured to retard the motion of the end effectors 2606, 2608 toward each other in response to a determination, based on the strength of the fields emitted and detected by the sensors 2614, 2616, that the end effectors 2606, 2608 are within a threshold distance of each other. An alert can be generated for notifying the operator that the end effectors 2606, 2608 have slowed or stopped moving. The controller can be configured to allow the operator to move the end effectors closer toward each other. In this manner, a full range of motion is possible while also reducing the chances of the end effectors colliding with each other, other objects, or the patient.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical systems can also be used in open surgical procedures. As used herein, a surgical access point is a point at which the slave tool enters a body cavity through a tissue surface, whether through a cannula in a minimally invasive procedure or through an incision in an open procedure.

Through manipulation of a control system such as the control system 315 discussed above, a user can control one or more parts of a surgical system incorporating the robotic arm 420 and the tool assembly 430 discussed above. For example, a user can control the robotic arm 420 that supports and moves the associated tool assembly 430 along one or more mechanical degrees of freedom. Input from the user can control the tool driver 440, which can assist with controlling features associated with the tool assembly 430. During a minimally-invasive surgery, the user can manipulate the robotic arm 420 to introduce the tool assembly 430 through the entry guide 432 (e.g., a cannula mount or cannula). The user can thus direct insertion of the shaft 436 of the tool assembly 430 and the end effector 438 through the entry guide 430 and into the body of a patient. Through interaction between the user and the control system, the tool assembly 430 can be oriented and positioned such that tissue is between the first and second jaws 502, 504 of the end effector 438. Articulation can be caused by a user manipulating the surgical system to cause movement of the end effector 438. When tissue has been positioned between the jaws 502, 504, a user can actuate the control system to cause the jaws 502, 504 to close on tissue positioned therebetween and/or cause the sled 530 to be advance through the end effector 438, cut tissue engaged between the jaws 502, 504, and fire at least one staple into engaged tissue.

During movement of the sled 530, a travel speed of the sled 530 relative to the end effector 438 can be calculated, for example by the surgical system and/or the control system 315 and/or a user. Through monitoring positions of the sled 530 using the first, second, and/or third visual indicators as described above, for example by comparing a first position of the sled 530 to a second position of the sled 530, the surgical system can determine the travel speed of the sled 530 and either decrease or increase the travel speed thereof, depending on the desired outcome as described above. For example, if the travel speed exceeds a set threshold, the sled 530 can be slowed. If the travel speed is less than a set threshold, the sled 530 can be sped up. A user can input a desired speed threshold and/or desired outcome, or the surgical system can be preset with the desired speed threshold and/or desired outcome. After the sled 530 has completed traveling between the distal and proximal ends of the end effector 438 and has returned to a starting position, the user can use the control system to reposition the end effector and complete another firing of the sled 530 and/or the user can use the control system to retract the end effector from the patient.

There are several general aspects that apply to the various descriptions herein. For example, at least one surgical end effector is shown and described in various figures. An end effector is the part of a surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical systems described herein.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 21:
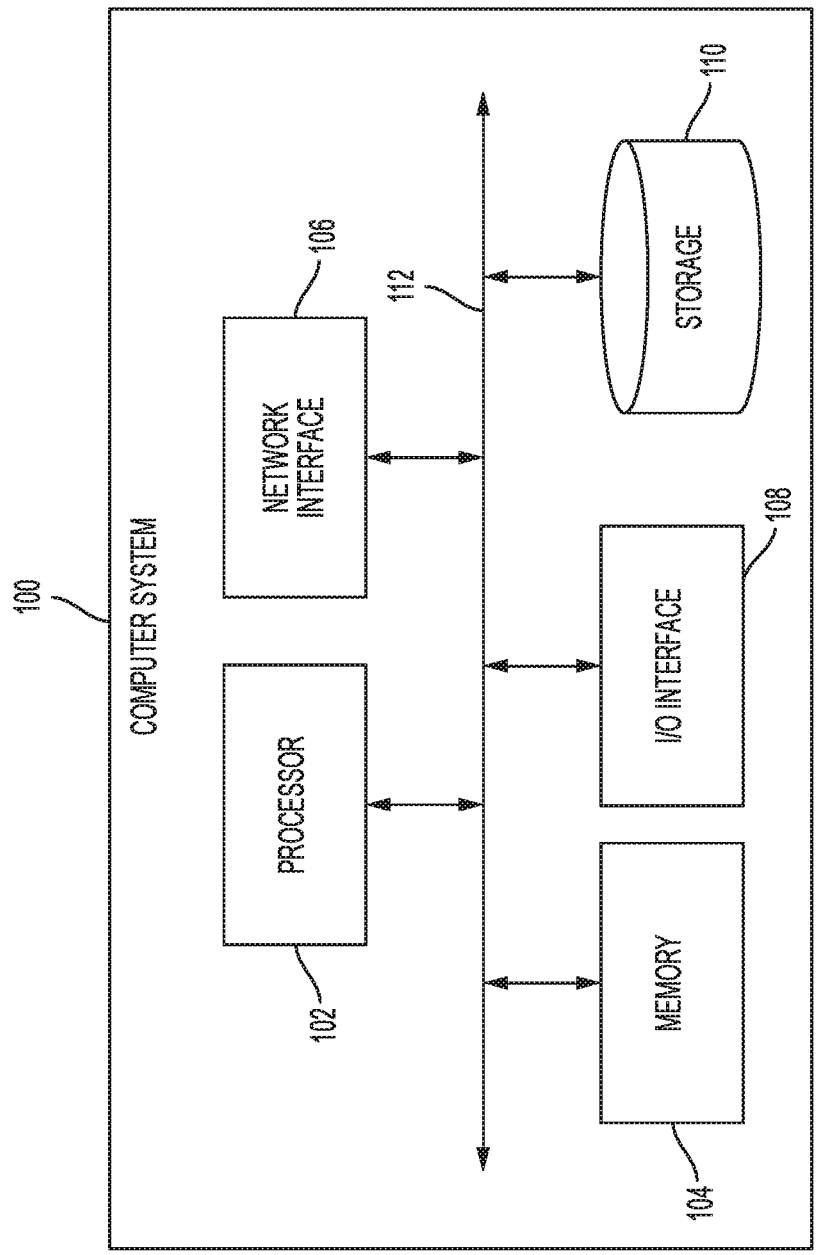
FIG. 21 is a schematic depiction of one exemplary embodiment of a computer system having one or more features consistent with the present description.

FIG. 21 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 21 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
transmitting by a controller on a surgical robotic system input instructions to an electromechanical tool to thereby actuate the tool;
visually obtaining by the surgical robotic system information from a visual indicator on the tool indicative of a length scale; and
transmitting by the controller altered input instructions to the electromechanical tool based on the visually obtained information when the visually obtained information differs from the input instructions.

2. The method of claim 1, wherein the input instructions cause a cutting element to travel through an end effector of the tool at a first travel speed, and wherein the visual indicator indicates an actual travel speed of the cutting element.

3. The method of claim 2, wherein the altered input instructions comprise a reduced travel speed if the actual travel speed exceeds a threshold travel speed.

4. The method of claim 1, wherein the visual indicator comprises at least one marking formed on an end effector of the tool and configured to indicate a length scale of the tool.

5. The method of claim 1, wherein the surgical robotic system comprises a camera to obtain information from the visual indicator.

6. The method of claim 1, wherein the visual indicator comprises openings along at least one of first and second jaws of an end effector on the tool.

7. The method of claim 6, wherein the end effector has a proximity zone at a distal end thereof, and the controller reduces a speed of advancement of a cutting element through the end effector when the cutting element reaches the proximity zone.

8. A surgical method, comprising:
- transmitting by a controller on a surgical robotic system actuation instructions to a tool to thereby actuate an end effector on a distal end of the tool;
- visually obtaining by the surgical robotic system information from a first visual indicator on the tool and a second visual indicator on the end effector; and
- determining by the controller a location of the end effector relative to the tool based on the first and second visual indicators.

9. The method of claim 8, wherein the controller transmits altered actuation instructions to the tool based on the location of the end effector relative to the tool.

10. The method of claim 8, wherein the first and second visual indicators are indicative of a length scale, and if the visually obtained information differs from the actuation instructions, transmitting by the controller altered actuation instructions to the tool.

11. The method of claim 10, wherein the actuation instructions cause a cutting element to travel through the end effector of the tool at a first travel speed, and wherein the first and second visual indicators indicate an actual travel speed of the cutting element.

12. The method of claim 11, wherein the altered actuation instructions comprise a reduced travel speed of the cutting element if the actual travel speed exceeds a threshold travel speed.

13. The method of claim 12, wherein the controller calculates the actual travel speed of the cutting element based on locations of the first and second visual indicators over time.

14. The method of claim 10, wherein the actuation instructions cause a cutting element to travel through the end effector of the tool at a first travel speed, and wherein the first and second visual indicators indicate an actual location of the cutting element within the end effector.

15. The method of claim 14, wherein the controller compares the actual location of the cutting element moving through the end effector to an expected location based on the actuation instructions, and the altered actuation instructions alter a speed of the cutting element when the actual location does not correspond to the expected location.

16. The method of claim 8, wherein the second visual indicator comprises at least one marking formed on the end effector and configured to indicate a length scale of the tool.

17. The method of claim 8, wherein at least one of the first and second visual indicators comprises a grid pattern.

18. The method of claim 8, wherein the surgical robotic system comprises a camera to obtain information from the first and second visual indicators.

19. The method of claim 8, wherein the second visual indicator comprises openings along at least one of first and second jaws of the end effector.

20. The method of claim 8, wherein the end effector has a proximity zone at a distal end thereof, and the controller reduces a speed of advancement of a cutting element through the end effector when the cutting element reaches the proximity zone.

* * * * *